United States Patent
Lin

(10) Patent No.: US 6,988,999 B1
(45) Date of Patent: Jan. 24, 2006

(54) KNEE PAD ASSEMBLY HAVING AN UPPER PAD AND A LOWER PAD SEPARATELY CONNECTED TO THE UPPER PAD TO AVOID MOVEMENT IMPEDENCE TO THE PATELLA

(76) Inventor: Henkel Lin, No. 13, Lane 130, Kung-An Rd., Houli Hsiang, Taichung Hsien (TW)

( * ) Notice: Subject to any disclaimer, the term of this patent is extended or adjusted under 35 U.S.C. 154(b) by 0 days.

(21) Appl. No.: 10/930,812

(22) Filed: Sep. 1, 2004

(51) Int. Cl.
*A61F 5/00* (2006.01)

(52) U.S. Cl. .................. 602/26; 602/62; 2/24; 128/882
(58) Field of Classification Search .................. 602/26, 602/23, 62, 63, 64, 65, 75; 128/882, 845, 128/869, 883; 2/22, 24, 455, 911, 908
See application file for complete search history.

(56) References Cited

U.S. PATENT DOCUMENTS

| | | | |
|---|---|---|---|
| 4,240,414 A * | 12/1980 | Theisler | 602/26 |
| 4,387,709 A * | 6/1983 | Shen | 602/26 |
| 5,031,240 A * | 7/1991 | Nierhaus | 2/24 |
| 5,221,252 A * | 6/1993 | Caprio et al. | 602/63 |
| 5,411,037 A * | 5/1995 | Hess et al. | 128/882 |
| 5,538,500 A * | 7/1996 | Peterson | 602/62 |
| 5,944,682 A * | 8/1999 | Milana-Panopoulos | 602/62 |
| 6,063,048 A * | 5/2000 | Bodenschatz et al. | 602/62 |
| 6,223,350 B1 * | 5/2001 | McFarlane | 2/24 |
| 6,592,539 B1 * | 7/2003 | Einarsson et al. | 602/62 |
| 6,875,188 B2 * | 4/2005 | Chiang | 128/882 |

* cited by examiner

*Primary Examiner*—Fadi H. Dahbour
(74) *Attorney, Agent, or Firm*—Rosenberg, Klein & Lee

(57) ABSTRACT

A knee pad assembly includes a soft body, a top pad and a bottom pad. The body has a pair of straps each provided with a length regulator, a press extending from a connector which is slidable in the length regulator and a clamping finger integrally extending out from the press. The top pad has a first side securely connected to the soft body and a second side detachable from the soft body. The top pad has a first receiving hole to correspond to and receive therein the clamping finger of one of the two straps. The bottom pad has a first side securely connected to the soft body and a second side detachable from the soft body. The bottom pad has a second receiving hole to correspond to and receive therein the clamping finger of the other one of the two straps.

6 Claims, 5 Drawing Sheets

KNEE PAD ASSEMBLY HAVING AN UPPER PAD AND A LOWER PAD SEPARATELY CONNECTED TO THE UPPER PAD TO AVOID MOVEMENT IMPEDENCE TO THE PATELLA

BACKGROUND OF THE INVENTION

1. Field of the Invention

The present invention relates to a knee pad assembly, and more particularly to a knee pad assembly having an upper pad and a lower pad detachably connected to the upper pad so that movement of the knee, particularly the patella, will not be limited.

2. Description of Related Art

Recently, due to the mushrooming popularity of extreme sports, joint injuries arising from those sports have accordingly increased. Among such injuries, damage to knees is the most common due to the involvement of a lot of knee bending, twisting and stretching. Taking one extreme sport for example, in-line roller skaters often do a lot of turning, jumping and stopping in order to demonstrate different figures. While doing the demonstration, players' knees suffer from great stress, which not only wears out the cartilage but also brings potential danger to the patella from serious impact. In order to protect the patella and the muscle around the patella, knee pads have become extremely important to those whose performance involves a great deal of knee exercise, jumping and/or turning. The conventional knee pad assembly has a fixed structure such that when the user is bending, the upper portion of the knee pad assembly is away from the knee and can no longer provide protection to the knee. Furthermore, due to the fixed structure of the conventional knee pad assembly, the knee movement is interfered with by the knee pad assembly and is thus limited. As a result, the user of the conventional knee pad assembly can not comfortably demonstrate whatever figures is desired.

To overcome the shortcomings, the present invention tends to provide an improved knee pad assembly to mitigate the aforementioned problems.

SUMMARY OF THE INVENTION

The primary objective of the present invention is to provide an improved knee pad assembly to have an upper pad and a lower pad separate from the upper pad so that the user's knee movement is not limited.

Another objective of the present invention is that the upper pad has a first tongue extending out therefrom and overlapped with a second tongue of the lower pad.

Other objects, advantages and novel features of the invention will become more apparent from the following detailed description when taken in conjunction with the accompanying drawings.

DETAILED DESCRIPTION OF THE PREFERRED EMBODIMENT

Figure 1:
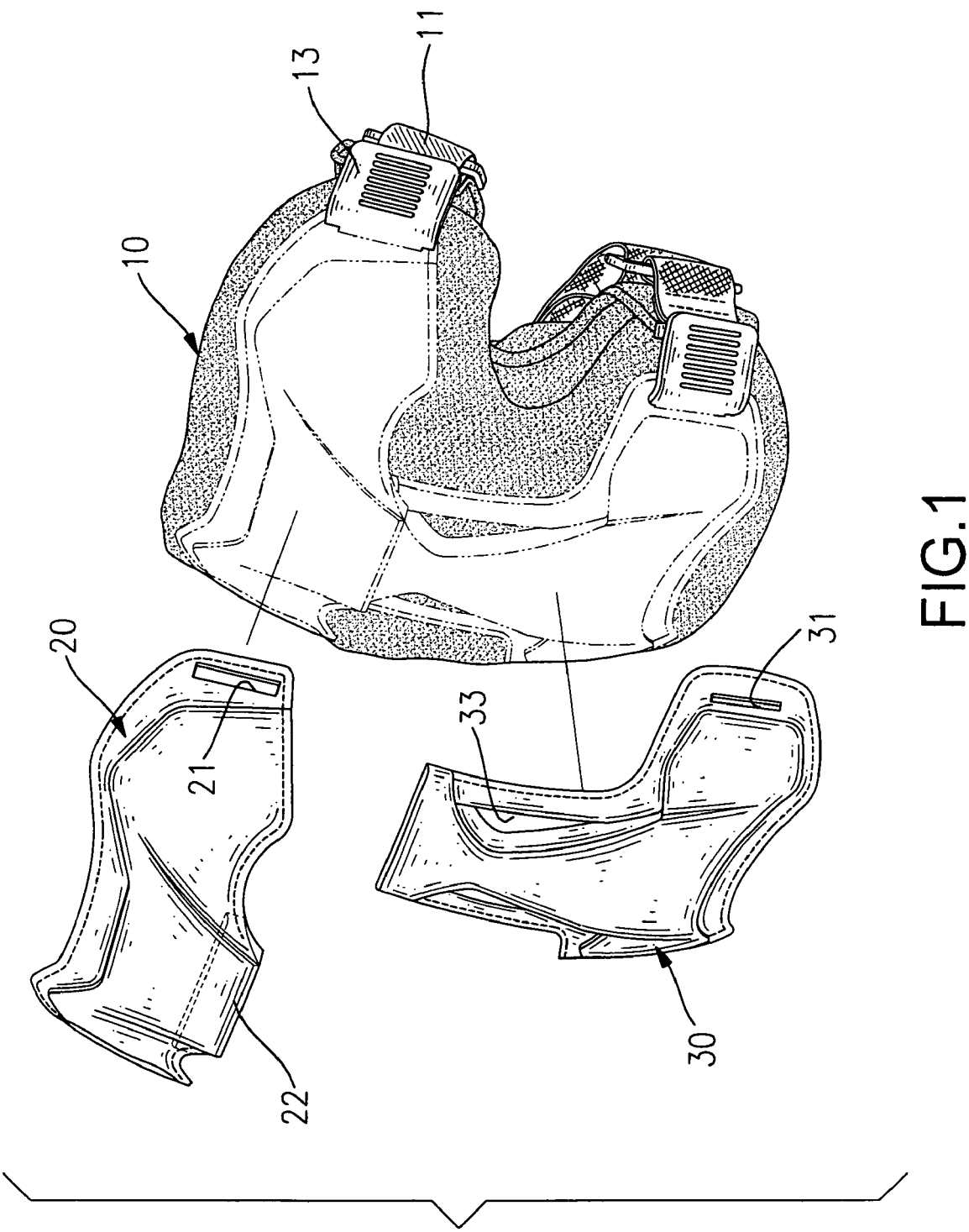
FIG. 1 is an exploded perspective view showing the structure of the present invention.
Figure 2:
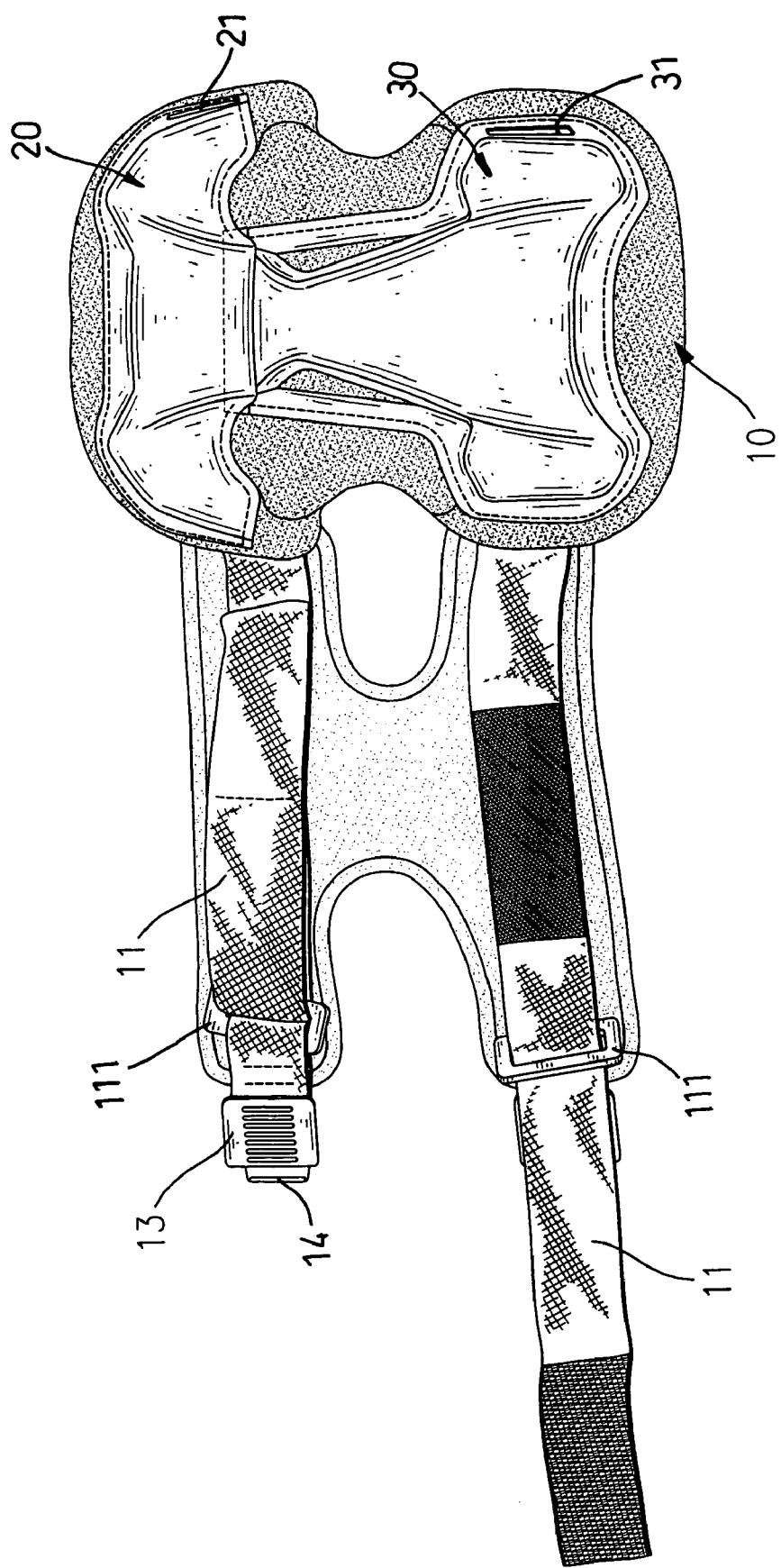
FIG. 2 is a plan view showing that the knee pad assembly of the present invention is extended.

With reference to FIGS. 1 and 2, the knee pad assembly in accordance with the present invention includes a body (10), an upper pad (20) and a lower pad (30).

The body (10) is made of soft and resilient material such as sponge or polymer. The body (10) has a pair of straps (11) each having a first end securely connected to the body (10) and a second end provided with a length regulator namely Velcro® such that the user is able to adjust the length of the strap (11) independently. From the depiction of FIG. 2, it is noted that the length regulator is provided with a male connector and a female connector such that after the strap (11) is extended over a connector (111) and folded back, the male connector and the female connector are able to engage with each other to secure the length of the strap (11). A press (13) is extended from the connector (111) and has a clamping finger (14) integrally formed with the press (13).

The upper pad (20) has a first side securely connected to the body (10) via a suitable process, e.g. sewing and a second side provided with a first receiving hole (21) corresponding to one of the clamping fingers (14). The lower pad (30) has a first side securely connected to the body (10) via a suitable process, e.g. sewing and a second side provided with a second receiving hole (31) corresponding to the other one of the clamping fingers (14) of the pair of straps (11). Furthermore, the top pad (20) has a first tongue (22) extending from a bottom of the top pad (20) and the bottom pad (30) has a second tongue (32) extending from a top of the bottom pad (30) to engage with the first tongue (22).

Figure 3:
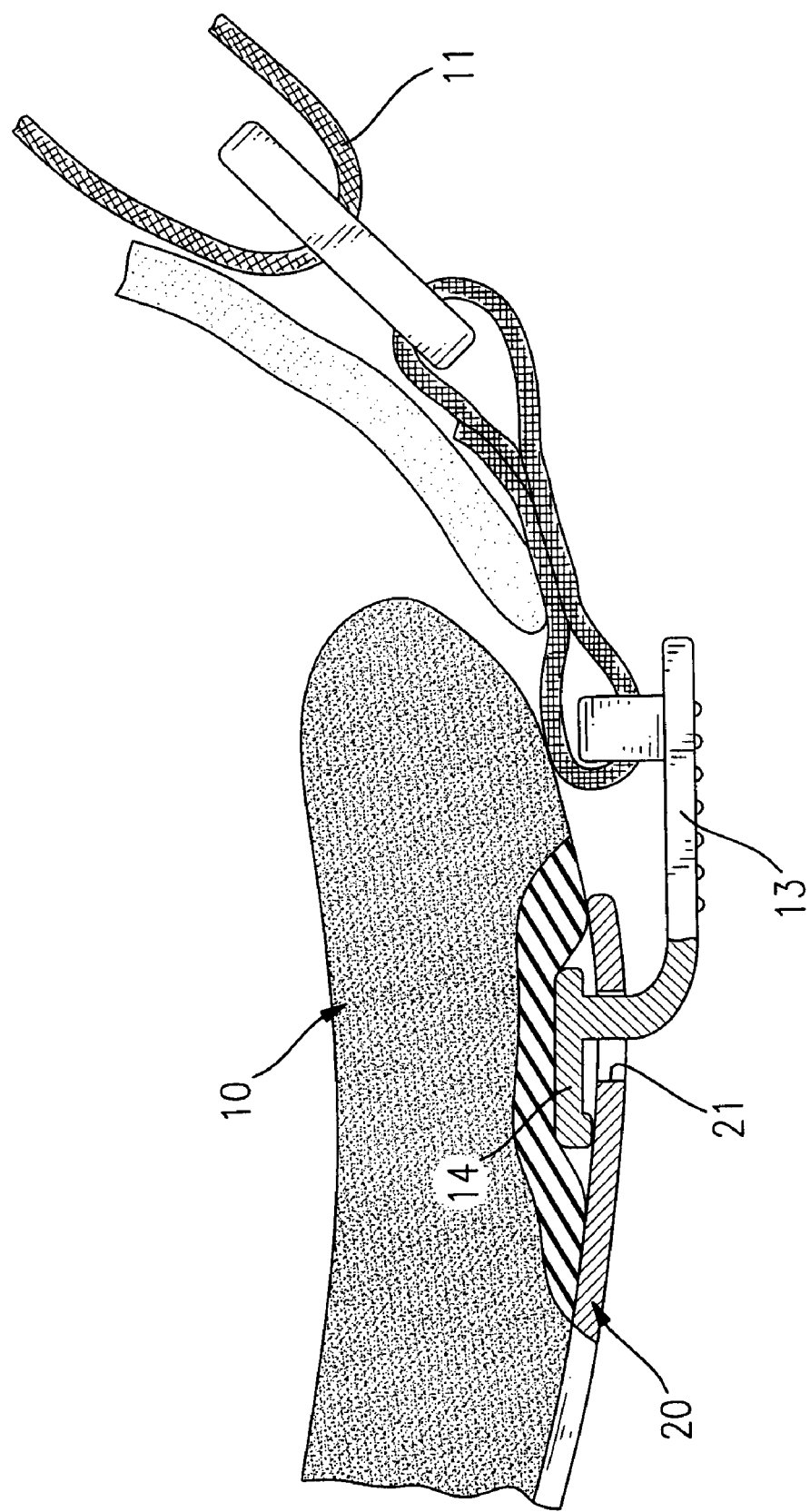
FIG. 3 is a partially enlarged cross sectional view showing the extension of the clamping finger into the receiving hole in the upper pad.

With reference to FIG. 3, it is noted that when the knee pad assembly of the present invention is assembled, the clamping finger (14) of each strap (11) is extended into the first receiving hole (21) of the top pad (20) and the second receiving hole (31) of the bottom pad (30). From the drawing, it is appreciated that the clamping finger (14) has a long side and a short side to form substantially a T shape. Therefore, to extend the clamping finger (14) into the first receiving hole (21) and the second receiving hole (31) of the top pad (20) and the bottom pad (30) respectively, the long side is first tilted for facilitating the extension of the long side into the first receiving hole (21). After the long side is extended into the first receiving hole (21), the clamping finger (14) is pushed along the first receiving hole (21) to allow the short side to align with the first receiving hole (21) such that the short side is able to extend into the first receiving hole (21). Thereafter, the user pulls the strap (11) backward to secure the location of the clamping finger (14) inside the first receiving hole (21). The extension of the clamping finger (14) into the second receiving hole (31) is the same as that of the first receiving hole (21) so that detailed description thereof is omitted.

Figure 4:
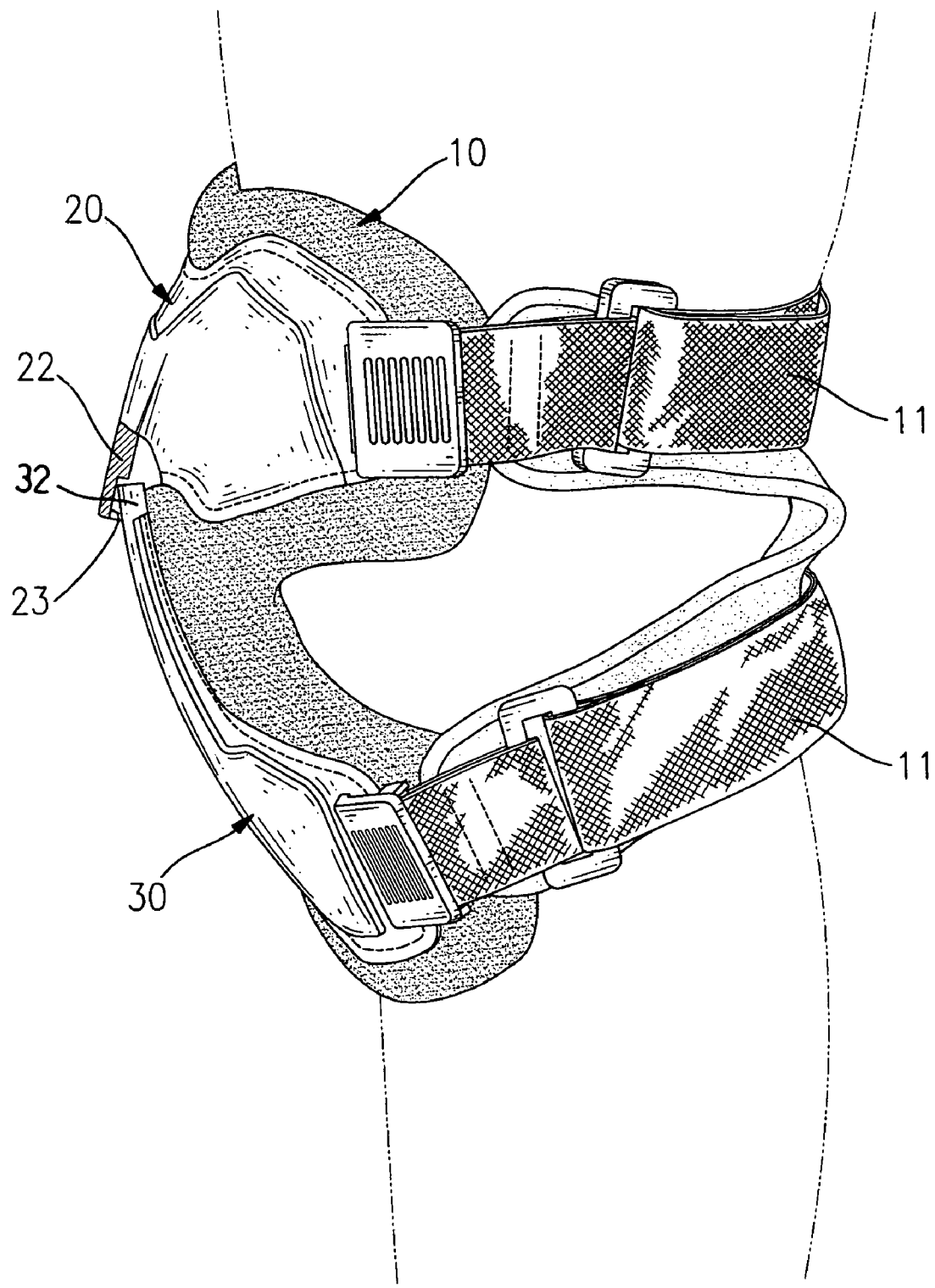
FIG. 4 is a schematic view showing that the knee pad assembly is employed to protect the user's knee.

With reference to FIG. 4, after the knee pad assembly is mounted around the user's knee (not numbered), the first tongue (22) overlaps the second tongue (32). In order to avoid too much extension of the first tongue (22) away from the second tongue (32), the first tongue (22) has a tapered thickness so as to form a step (23) on an inside of the first tongue (22). Therefore, when the first tongue (22) and the second tongue (32) are overlapped with one another, the first tongue (22) will not extend too much away from the bottom pad (30).

Figure 5:
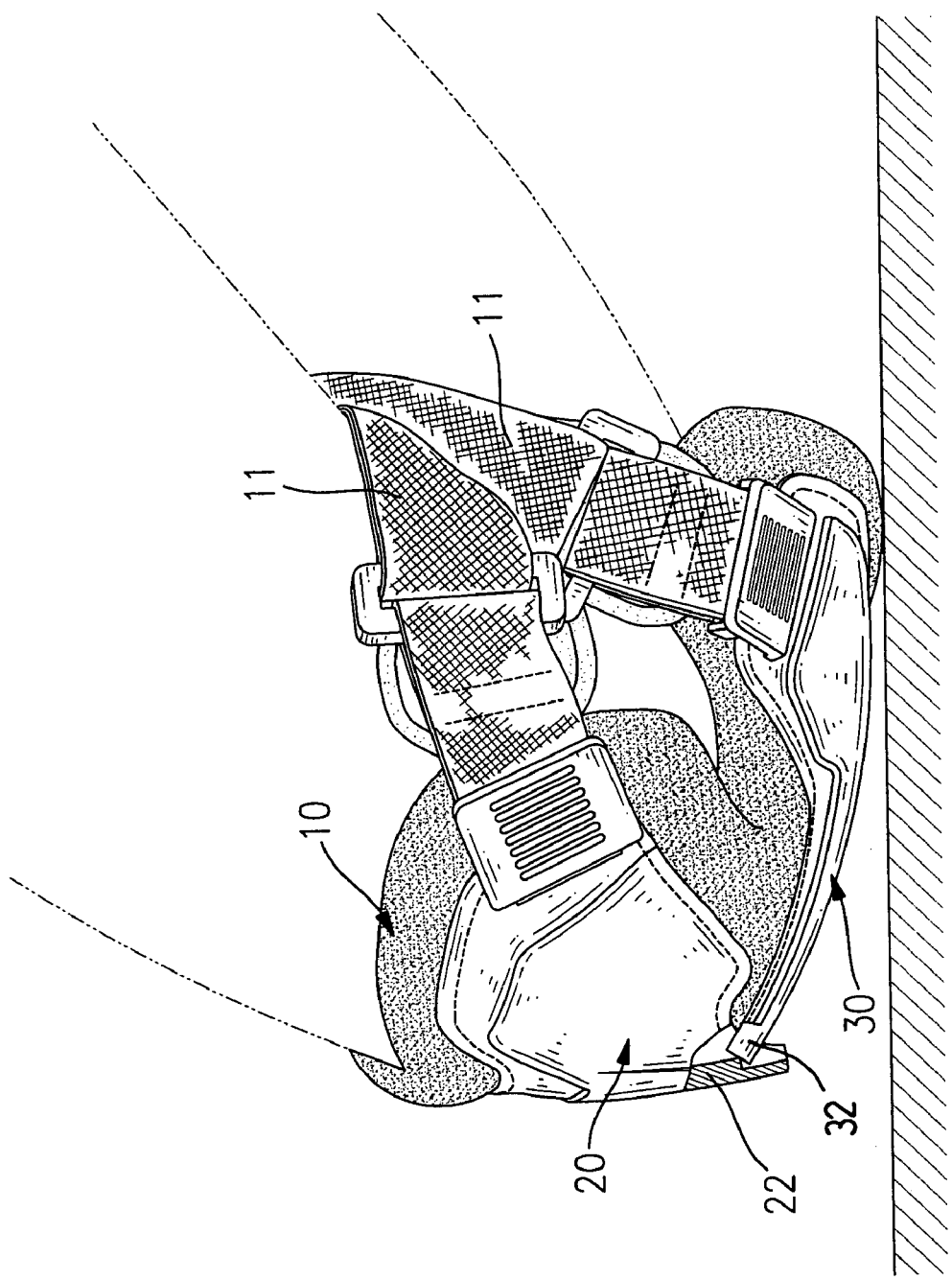
FIG. 5 is a schematic view showing that the folding of the knee will not be limited by the knee pad assembly of the present invention.

With reference to FIG. 5, because the top pad (20) and the bottom pad (30) are separated from each other, when the user's leg is bent at the knee, either the top pad (20) or the bottom pad (30) still abuts the user's knee to provide good protection and will not impede the knee movement.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A knee pad assembly comprising:
    a soft body having a pair of straps each provided with a length regulator to regulate length of the strap, a press extending from a connector which is slidable in the length regulator and a clamping finger integrally extending out from the press;
    a top pad having a first side securely connected to the soft body and a second side detachable from the soft body, the top pad having a first receiving hole to correspond to and receive therein the clamping finger of one of the two straps; and
    a bottom pad having a first side securely connected to the soft body and a second side detachable from the soft body, the bottom pad having a second receiving hole to correspond to and receive therein the clamping finger of the other one of the two straps.

2. The knee pad assembly as claimed in claim 1, wherein the top cover has a first tongue extending downward from a bottom of the top pad, the bottom pad has a second tongue extending upward from a top of the bottom pad to engage with the first tongue.

3. The knee pad assembly as claimed in claim 2, wherein the first tongue has a tapered thickness.

4. The knee pad assembly as claimed in claim 2, wherein the first tongue and the second tongue are overlapped with each other.

5. The knee pad assembly as claimed in claim 3, wherein the clamping finger has a long side and a short side to form substantially a T shape.

6. The knee pad assembly as claimed in claim 4, wherein the clamping finger has a long side and a short side to form substantially a T shape.

* * * * *